United States Patent [19]

Kardys

[11] Patent Number: 4,536,573
[45] Date of Patent: Aug. 20, 1985

[54] PROCESS AND INTERMEDIATES FOR PRODUCTION OF BENZOTHIAZINE CARBOXAMIDES

[75] Inventor: Joseph A. Kardys, Groton, Conn.

[73] Assignee: Pfizer Inc., New York, N.Y.

[21] Appl. No.: 609,126

[22] Filed: May 11, 1984

Related U.S. Application Data

[60] Division of Ser. No. 488,208, Apr. 25, 1983, Pat. No. 4,469,866, which is a continuation-in-part of Ser. No. 389,119, Jun. 17, 1982, abandoned, which is a continuation-in-part of Ser. No. 289,390, Aug. 3, 1981, abandoned.

[51] Int. Cl.³ ............... C07D 401/12; C07D 413/12; C07D 417/12
[52] U.S. Cl. ...................................................... 544/49
[58] Field of Search .......................................... 544/49

[56] References Cited

U.S. PATENT DOCUMENTS

| | | | |
|---|---|---|---|
| 3,591,584 | 7/1971 | Lombardino | 544/49 |
| 3,853,862 | 12/1974 | Lombardino | 260/243 R |
| 3,891,637 | 6/1975 | Lombardino | 260/243 R |
| 4,289,879 | 9/1981 | Lombardino | 544/49 |
| 4,309,427 | 1/1982 | Lombardino | 424/246 |

Primary Examiner—John M. Ford
Attorney, Agent, or Firm—Connolly and Hutz

[57] ABSTRACT

A novel compound of the formula

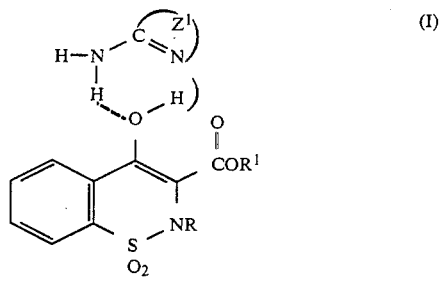

wherein R is hydrogen, benzyl or $(C_1-C_3)$alkyl; $R^1$ is benzyl or $(C_1-C_4)$alkyl and $Z^1$ taken together with $-C=N-$ forms a heterocyclic group Z where Z is 2-pyridyl, alkyl substituted-2-pyridyl, 2-thiazolyl, 2-thiazolyl substituted by one or two alkyl groups or 5-alkyl-3-isoxazolyl, each alkyl having from one to four carbon atoms; and a novel process employing the above compounds as intermediates for production of known anti-inflammatory agents of the formula

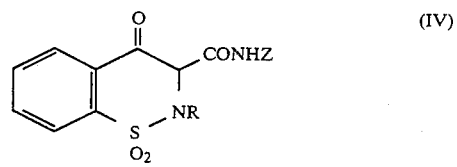

11 Claims, No Drawings

PROCESS AND INTERMEDIATES FOR PRODUCTION OF BENZOTHIAZINE CARBOXAMIDES

CROSS REFERENCE TO RELATED APPLICATION

This application is a division of application Ser. No. 488,208 filed Apr. 25, 1983, now U.S. Pat. No. 4,469,866, which in turn is a continuaton-in-part of copending application Ser. No. 389,119, filed June 17, 1982, now abandoned which in turn, is a continuation-in-part of Ser. No. 289,390, filed Aug. 3, 1981 and now abandoned.

BACKGROUND OF THE INVENTION

1. Field of the Invention

The invention relates to a novel class of hydrogen bond complex compounds of formula (I), below, which are useful as intermediates in an improved process for production of benzothiazine carboxamide anti-inflammatory agents.

2. Description of the Prior Art

Two methods for synthesis of N-substituted benzothiazine carboxamide anti-inflammatory agents are disclosed in U.S. Pat. No. 3,591,584. The first of these is used to prepare carboxamides in which the N-substituent is not an heterocyclic moiety. It comprises contacting an organic isocyanate, $R_3NCO$, wherein $R_3$ is, e.g. certain alkyl, phenyl or naphthyl groups, with a 4-oxo (or 3-oxo)1,2-benzothiazine to produce e.g., the compound of the formula

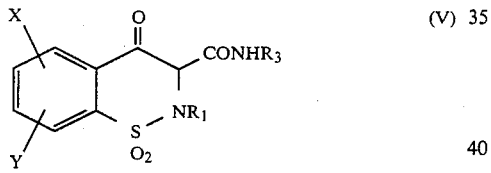

(V)

or the corresponding 3-oxo-4-carboxamide.

A second method is preferred for the preparation of those amides wherein the N-substituent is an heterocyclic moiety; it involves reaction of the corresponding carboxylic acid ester with the appropriate amine, $R_2NH_2$, where $R_2$ is a heterocyclic group, to produce the desired benzothiazine carboxamide, e.g.,

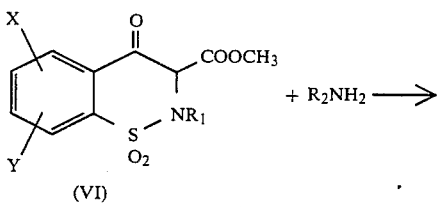

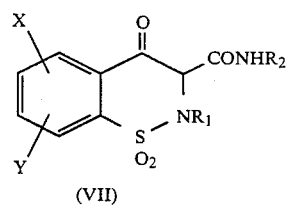

In U.S. Pat. No. 3,891,637 a process is disclosed whereby the N-heterocyclic amides of formula (VII) are obtained from the corresponding N-phenyl amides by a transamidation process.

U.S. Pat. No. 3,853,862 discloses a process for production of 4-oxo-1,2-benzothiazine-3-carboxamides of formula (VII) by cyclization of a benzenesulfonyl-glycineamide (III) in the presence of a metal hydride, e.g.,

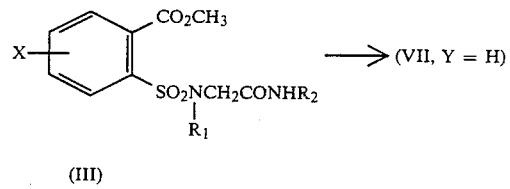

U.S. Pat. No. 4,289,879, issued Sept. 15, 1981, discloses a method for preparing piroxicam [4-hydroxy-2-methyl-N-(2-pyridyl)-2H-1,2-benzothiazine-3-carboxamide 1,1-dioxide] via the corresponding 3-(2-methoxyethyl) ester.

SUMMARY OF THE INVENTION

In accordance with the present invention, it has now been found that a novel class of hydrogen bond complex compounds of the formula

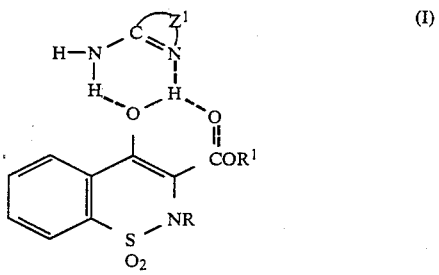

are valuable intermediates useful for production of 4-oxo-1,2-benzothiazine-3-carboxamide-1,1-dioxide anti-inflammatory agents of the formula (IV) by a novel process having significant advantages over the prior art.

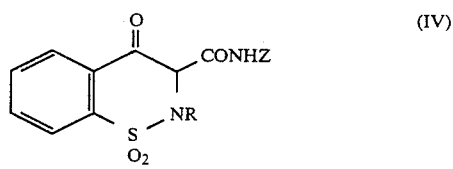

In the above compounds R is hydrogen, benzyl or alkyl having from one to three carbon atoms; $R^1$ is benzyl or alkyl having from one to four carbon atoms; and $Z^1$ taken together with —C═N—, forms a heterocyclic group Z, where Z is 2-pyridyl, alkyl substituted-2-pyridyl, 2-thiazolyl, 2-thiazolyl substituted by one or two alkyl groups, or 5-alkyl-3-isoxazolyl, each alkyl having from one to four carbon atoms.

The present invention also provides the above mentioned process for production of the above compounds of formula (IV) which comprises the steps of (a) reacting a 4-oxo-1,2-benzothiazine-3-carboxylic acid ester of the formula

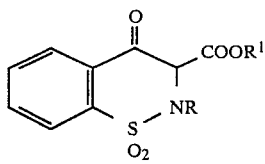

with an equimolar amount of an amine of the formula $ZNH_2$ in the presence of a reaction inert organic solvent and at a temperature of from 0° to 110° C. to provide an intermediate of formula (I), as defined above;

(b) heating the intermediate obtained in (a) in the presence of a reaction inert organic solvent at a temperature of from about 120° to 200° C. to eliminate $R^1OH$ where $R^1$ is as defined above.

In the compounds of the invention of formula (I) and in the process of the invention particularly preferred values for substituents R, $R^1$ and Z are:

R is alkyl having from one to three carbon atoms,
$R^1$ is alkyl having from one to four carbon atoms, and
Z is 2-pyridyl, 2-thiazolyl, 5-methyl-3-isoxazolyl, 6-methyl-2-pyridyl or 4,5-dimethyl-2-thiazolyl.

More particularly preferred values for the above substituents are:

R is methyl,
$R^1$ is methyl or ethyl, and
Z is 2-pyridyl, 2-thiazolyl or 5-methyl-3-isoxazolyl.

The most particularly preferred compound of the invention is of formula (I) where R and $R^1$ are each methyl and Z is 2-pyridyl. The corresponding anti-inflammatory agent of formula (IV) provided by the invention process is known generically as "piroxicam". See, e.g., Wiseman, Roy. Soc. Med. Int. Cong. Symp. Ser. 1, 11–23 (1978).

The invention process has advantages of improved yield and increased productivity which affords a significantly greater weight of product of formula (IV) per volume of solvent. The product of formula (IV) obtained by the invention process is also of improved purity. A further advantage of the invention process is that the mother liquors can be recycled repeatedly to the next batch with good results.

Isolation of the intermediate of formula (I) in the process of the invention affords an additional purification, not possible in the prior art process. Thus, in the instant process, one may use starting materials of lesser purity since they are purified by isolation of the intermediate compound (I). This is a distinct advantage since an impure amine $ZNH_2$ can be employed without reduction of purity of the anti-inflammatory agent (IV). Furthermore, it is known in the art that amines, of the formula $ZNH_2$ as defined above are difficult to purify by prior art methods.

DETAILED DESCRIPTION OF THE INVENTION

The compounds of the invention of the formula (I) are obtained by contacting approximately equimolar amounts of 4-oxo-1,2-benzothiazine-3-carboxylic acid ester of formula (II) and the appropriate amine, $ZNH_2$, where Z is as previously defined. The reaction is carried out in the presence of a reaction inert organic solvent at a temperature of from about 0° to 110° C. and a reaction time of up to twenty-four hours. An especially preferred range of temperature for this reaction is from about 20° to 90° C., at which temperature the reaction is ordinarily complete in from a few minutes to a few hours, for example, 15 minutes to about four hours. The product of formula (I) is then isolated, if desired, e.g., by cooling the reaction mixture to room temperature or below, filtering to collect the precipitated solid, and drying.

A reaction inert organic solvent as defined herein is one that does not react appreciably with either the starting materials or the products of the reaction under the reaction conditions employed, and is capable of dissolving at least a substantial portion of the starting materials at or below the reaction temperature. Further, said solvent is one from which the desired product is readily recoverable by standard techniques known to one of skill in the art. Examples of reaction inert organic solvents which can be employed in preparing the desired compounds of formula (I) are hydrocarbons such as benzene, toluene, the xylenes, ethylbenzene, tetralin and decalin; halogenated hydrocarbons such as chloroform, methylene dichloride, ethylene dichloride, ethyl bromide and ethylene dibromide; ketones such as acetone and methylethylketone, ethers such as ethyl ether, tetrahydrofuran, 1,2-dimethoxyethane and diethyleneglycol dimethylether; dialkylamides such as dimethylformamide, dimethylacetamide and N-methyl-2-pyrrolidinone; dimethylsulfoxide and acetonitrile. Particularly preferred are the above solvents having an atmospheric boiling point at least as high as the maximum reaction temperature employed. Especially preferred is commercial mixed xylenes for reasons of economy and efficiency.

Initial studies on the isolated products obtained by contacting an ester of formula (II) with an amine, $ZNH_2$, under the conditions of step (a) of the invention process, suggested a structure having covalent bonding between the ester and amine to form a hemiorthoamide structure analogous to the classical intermediate postulated for such reactions, i.e.,

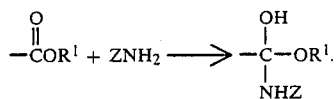

However, continued studies have now conclusively shown the intermediates to be 1:1 molar adducts with extensive hydrogen bonding as depicted in formula (I). The infrared, $^{13}$C-NMR and $^1$H-NMR spectral evidence, as well as X-ray crystallography studies, are consistent with the structure (I).

As mentioned above, the compounds of formula (I) are useful as intermediates in production of anti-inflammatory agents of the formula (IV) by elimination of $R^1OH$. The latter reaction is also carried out in the presence of one of the particularly preferred reaction inert organic solvents, defined above, but at an elevated temperature in order to drive out the alcohol generated in the reaction. A preferred temperature for this reaction is from about 120° to 200° C. and especially preferred is about 135° to 145° C.

The reaction inert organic solvents that can be used in production of compounds of formula (IV) by the above reaction are the same as those given above for the production of the invention compounds of formula (I), except those which boil at a temperature substantially below the preferred range of temperature, and would thus require the use of high pressure equipment. Especially preferred solvents for this reaction are toluene, the xylenes, ethylbenzene, tetralin and decalin; and most especially preferred is mixed xylenes for reasons of economy and efficiency. Of course, as one of skill in the art will recognize, the mixed xylenes also have the advantage of having a boiling point within the especially preferred range of temperature, a feature which facilitates temperature regulation and removal of by-product alcohol, $R^1OH$.

In the first step of the invention process the formation of a solid intermediate product of formula (I) provides a purification method not possible with the prior art process in which the ester (II) and amine $ZNH_2$ are reacted to form (IV) directly. Thus, relatively impure starting materials of formula (II) and $ZNH_2$ can be employed in the instant process and purification effected by isolation of the novel intermediate of formula (I) prior to its conversion to the anti-inflammatory agent, (IV). For example, this feature allows for the use of a Technical Grade (<97% pure) 2-aminopyridine in the instant process with significant cost and safety advantages since this compound is extremely hazardous and malodorous, making it both difficult and costly to purify by known methods.

A further advantage of the present process is that the desired product (IV) can be obtained in improved yield and with greater throughput than is possible with the most favorable prior art process, i.e., the method of U.S. Pat. No. 3,591,584 described above for production of benzothiazine-3-carboxamides via the corresponding 3-carboxylic acid ester and a heterocyclic amine such as $ZNH_2$ where Z is as defined herein. In the prior art method when total concentration of reactants greater than about 3 g per 100 ml of solvent are employed, the reaction mixture produces relatively high levels of decomposition products and color bodies, which makes isolation of the desired product of formula (IV) difficult and renders an impure product not suitable for pharmaceutical use without further costly purification steps.

The present process, however, can be carried out in such a manner that the throughput can be increased in Step (b) to 6-8 grams per 100 ml, or higher, without sacrificing yield of product or its purity. This is accomplished by isolating the novel intermediate compound of formula (I) obtained in Step (a) and adding it in portions to the heated solvent mixture employed in Step (b) to eliminate the elements of $R^1OH$ and form the product (IV) in high yield and purity.

Yet another advantage that can be demonstrated with the invention process is that the mother liquors can be recycled repeatedly to the next reaction run. High yield and high purity of product is observed after repeated recycling of mother liquors in the instant process, thus avoiding loss of product retained in the mother liquor. By contrast, when recycling is carried out with the prior art process, accumulation of impurities becomes so great after a few recycles of mother liquor that the desired product can not be isolated or can only be isolated with great difficulty.

The following Examples are illustrative of the claimed invention. The following abbreviations are used for NMR peak multiplicity: s, singlet; d, doublet; t, triplet; d of t, doublet of triplets; q, quartet; m, multiplet.

EXAMPLE 1

Crystalline Compound of Formula (I), $R=R^1=CH_3$, Z=2-pyridyl

Under a nitrogen atmosphere to a solution of 120 g (0.446 mole) methyl 3,4-dihydro-2-methyl-4-oxo-2H-1,2-benzothiazine-3-carboxylate-1,1-dioxide in 300 ml xylene is added 48 g (0.510 mole) 2-aminopyridine. The mixture is heated to 80° C. with vigorous stirring, held at this temperature for two hours, cooled to room temperature, filtered and dried to obtain 158.6 g (98%) of the desired complex as yellow crystals, m.p. 132°–133° C.

Titration of a sample with 0.50N hydrochloric acid in 2:1 (by volume) methanol/water gave a neutralization equivalent of 367.6 (theory 363). Mass spectrum (m/e) parent peak at 331. Infrared spectrum (KBr) cm$^{-1}$: strong carbonyl absorption at 1675 and 1660 cm$^{-1}$.

Analysis: Calc'd for $C_{16}H_{17}N_3O_5S$: C, 52.89; H, 4.72; N, 11.56. Found: C, 52.88; H, 4.77; N, 11.66.

| 250 MHz $^1$H—NMR (CDCl$_3$) ppm (delta): | | |
|---|---|---|
| ppm | Multiplicity | Integral |
| 8.05 | m | 2 |
| 7.88 | m | 1 |
| 7.73 | m | 2 |
| 7.44 | d of t | 1 |
| 6.60 | d of t | 1 |
| 6.52 | d | 1 |
| 3.97 | s | 3 |
| 2.96 | s | 3 |

| $^{13}$C—NMR (DMSO): | | |
|---|---|---|
| Line | ppm | Multiplicity |
| 1 | 167,988 | s |
| 2 | 158,917 | s |
| 3 | 158,449 | s |
| 4 | 146,076 | d |
| 5 | 137,673 | d |
| 6 | 134,902 | s |
| 7 | 133,005 | d |
| 8 | 132,743 | d |
| 9 | 128,662 | s |
| 10 | 126,557 | d |
| 11 | 123,381 | d |
| 12 | 111,736 | d |
| 13 | 109,330 | s |
| 14 | 108,609 | d |
| 15 | 52,458 | q |
| 16 | 38,489 | q |

For comparison with $^{13}$C-NMR spectra of piroxicam and methyl 3,4-dihydro-2-methyl-4-oxo-2H-1,2-benzothiazine-3-carboxylate 1,1-dioxide, see Whipple, *Organic Magnetic Resonance*, 10, 23 (1977).

Addition of 1.0 equivalent of methyl 3,4-dihydro-2-methyl-4-oxo-2H-1,2-benzothiazine-3-carboxylate 1,1-dioxide to a sample of the above product in dimethylsulfoxide produced an increase in 11 of the lines of the $^{13}$C-NMR spectrum, with slight changes in chemical shift. This clearly shows that in solution there is a rapid exchange during the NMR time scale.

For X-ray crystallography study the product obtained above is allowed to crystallize from acetone at room temperature to yield large yellow cubic crystals, M.P. 132° C. (sharp).

From the X-ray data it is concluded that:
(a) the enolic proton is hydrogen bonded to the ring nitrogen of 2-aminopyridine and to the ester carbonyl oxygen atom;
(b) one of the protons of the 2-amino group is bonded to the enolic oxygen atom;
(c) the other 2-amino proton is hydrogen bonded to an oxygen atom of the sulfone of another molecule of the product.
(d) the structure of the compound is represented by the formula below

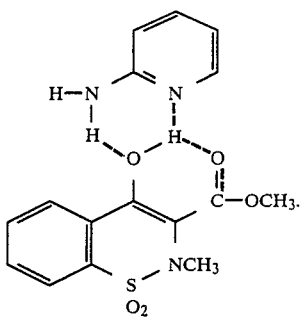

(I, R=R¹=CH₃, Z¹ completes a 2-pyridyl ring)

EXAMPLE 2

To 13 ml acetone is added 2.69 g (0.01 mole) methyl 3,4-dihydro-2-methyl-4-oxo-2H-1,2-benzothiazine-3-carboxylate-1,1-dioxide and 0.94 g (0.01 mole) 2-aminopyridine and the mixture warmed to affect solution. The yellow solution is refrigerated until precipitation is complete, filtered and the yellow crystals dried to afford the compound (I), R=R¹=CH₃, Z=2-pyridyl, m.p. 132°–133° C., in 84% yield.

The above procedure is repeated on the same scale, but employing a wide variety of reaction inert organic solvents in place of acetone. The results are summarized in the table, below.

| Solvent | Volume, ml | Reaction Temp., °C. | % Yield | Comment |
|---|---|---|---|---|
| CH₂Cl₂ | 50 | 30° | 98 | crystals washed with hexane |
| CHCl₃ | 20 | warm to dissolve | 81 | crystals washed with hexane |
| CH₃CO₂C₂H₅ | 20 | warm to dissolve | 88 | — |
| CH₃CN | 10 | warm to dissolve | 89 | crystals washed with hexane |
| tetrahydrofuran | 15 | warm to dissolve | 80 | — |
| CH₃COCH₃ | (15) | reflux (56°) | 94 | product precipitated with hexane |

When the above reaction is repeated in acetone as solvent, but with a molar excess of either the methyl ester or 2-aminopyridine reactant, the same product is obtained as yellow crystals, m.p. 132°–134° C. When the ester reactant (II) is used in excess, it sometimes forms as white crystals adhering to the sides of the flask which are readily separated from the yellow crystals of formula (I).

When the procedure is repeated in tetrahydrofuran at 0° C. or in toluene at 110° C., the results are substantially the same.

EXAMPLE 3

When the procedures of Examples 1 or 2 are repeated but the methyl 3,4-dihydro-2-methyl-4-oxo-2H-1,2-benzothiazine-3-carboxylate 1,1-dioxide is replaced with an appropriate compound of formula (II), the corresponding compound of formula (I) is obtained as shown below.

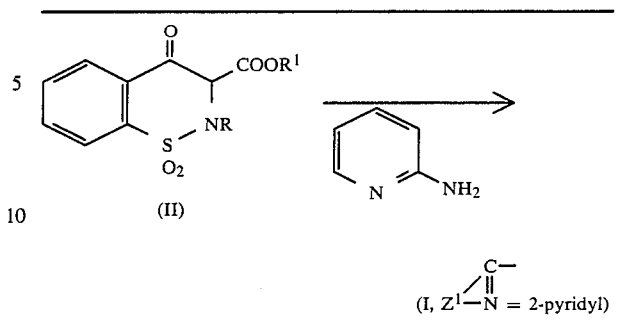

(I, Z¹—N = 2-pyridyl)

| R | R¹ |
|---|---|
| CH₃ | C₂H₅ |
| CH₃ | n-C₃H₇ |
| C₂H₅ | i-C₃H₇ |
| C₆H₅CH₂ | n-C₄H₉ |
| CH₃ | i-C₄H₉ |
| i-C₃H₇ | n-C₄H₉ |
| n-C₃H₇ | sec-C₄H₉ |
| C₆H₅CH₂ | CH₃ |
| H | n-C₄H₉ |
| H | C₂H₅ |

EXAMPLE 4

Crystalline Compound of Formula (I), R=R¹=CH₃,

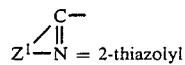
Z¹—N = 2-thiazolyl

To a mixture of 2.69 g (10 mmole) methyl 3,4-dihydro-2-methyl-4-oxo-2H-1,2-benzothiazine-3-carboxylate-1,1-dioxide and 50 ml xylene stirred under nitrogen is added 1.05 g (10.5 mmole) 2-aminothiazole. The mixture is heated at 85°–90° C. for 3 hours, cooled to room temperature, filtered and the brown, crystalline product dried in vacuo to obtain the title compound, 2.3 g (62.3%), m.p. 131°–142° C.

The crystalline product is dissolved in 20 ml of methylene chloride, decolorized by addition of activated charcoal and then filtered. Addition of the filtrate to hexane with good stirring, granulating for one hour and then filtering gave a white crystalline product; m.p. 140°–145° C., 1.35 g.

When the above procedure is repeated but employing acetone, methylene chloride, ethyl ether, ethylene dibromide, 1,2-dimethoxyethane, benzene, dimethylformamide, dimethylacetamide, ethylbenzene, toluene or decalin as solvent at a temperature of from 0°–110° C. for 2–24 hours, the desired product of formula (I) is similarly obtained.

EXAMPLE 5

The following compounds of formula (I) are obtained by the procedures of Examples 1–4 by employing the appropriate starting materials of formula (II) and ZNH₂.

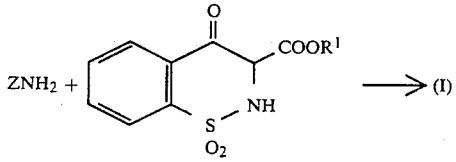

| R | R¹ | Z = Z¹—N⟨C=⟩ |
|---|---|---|
| CH₃ | C₆H₅CH₂ | 2-pyridyl |
| CH₃ | CH₃ | 2-pyridyl |
| H | C₂H₅ | 5-methyl-2-pyridyl |
| C₂H₅ | n-C₃H₇ | 2-pyridyl |
| n-C₃H₇ | n-C₄H₉ | 2-thiazolyl |
| n-C₄H₉ | C₆H₅CH₂ | 5-methyl-2-thiazolyl |
| CH₃ | i-C₃H₇ | 4-ethyl-2-thiazolyl |
| C₆H₅CH₂ | CH₃ | 5-n-butyl-2-thiazolyl |
| CH₃ | CH₃ | 5-methyl-3-isoxazolyl |
| C₂H₅ | CH₃ | 5-methyl-2-pyridyl |
| CH₃ | CH₃ | 4-methyl-2-pyridyl |
| CH₃ | CH₃ | 6-methyl-2-pyridyl |
| CH₃ | C₂H₅ | 6-n-propyl-2-pyridyl |
| CH₃ | CH₃ | 6-i-butyl-2-pyridyl |
| C₂H₅ | CH₃ | 5-ethyl-3-isoxazolyl |
| C₂H₅ | CH₃ | 5-isopropyl-3-isoxazolyl |
| H | CH₃ | 5-n-butyl-3-isoxazolyl |
| H | CH₃ | 4-methyl-2-thiazolyl |
| CH₃ | CH₃ | 4,5-dimethyl-2-thiazolyl |
| CH₃ | CH₃ | 4,5-di-n-butyl-2-thiazolyl |

EXAMPLE 6

Standard Method for Preparation of Piroxicam

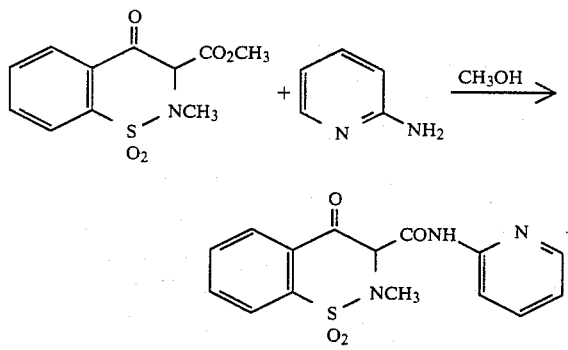

To a five liter flask equipped with thermometer, packed distillation column, condenser, and stirrer, under a nitrogen atmosphere is added 3300 ml mixed xylenes, 80 g (0.297 mole) methyl 3,4-dihydro-2-methyl-4-oxo-2H-1,2-benzothiazine-3-carboxylate-1,1-dioxide, 32 g (0.340 mole) 2-aminopyridine and 8 g of activated carbon (Darco G-60* or Darco KBB*). The mixture is heated at reflux (ca. 140° C.) for 28 hours while slowly distilling off methanol and xylene at a rate of about 25 ml per hour for the first 8 hours, then at a rate of 5–10 ml per hour for the remaining reflux period, while adding fresh xylene to maintain a reaction volume of about 3500 ml. After 28 hours, the reaction mixture is cooled slightly (~100° C.) and filtered to remove carbon. The carbon cake was washed with warm xylene (100 ml), the filtrate and washings cooled slowly under a nitrogen atmosphere with rapid stirring to 25°–50° C. Stirring was continued for one hour to allow for complete crystallization. The crystals were collected by filtration, the mother liquor concentrated to about 1500 ml, cooled under nitrogen to 0°–5° C., filtered, the cake washed with 100 ml cold xylene and the crystals dried under vacuum below 60° C. for several hours. The yield is 76.7–84.6 g (78–86% of theory). Average throughput 24.4 g/liter of solvent.

*A Registered Trademark of ICI America, Inc.

EXAMPLE 7

Improved Piroxicam Process Employing the Intermediate

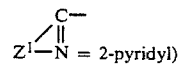

A. To a one liter flask purged with nitrogen is added 300 ml mixed xylenes, 120 g (0.446 mole) methyl 3,4-dihydro-2-methyl-4-oxo-2H-1,2-benzothiazine-3-carboxylate-1,1-dioxide and 48 g (0.510 mole) 2-aminopyridine. The mixture is heated to 90° C., stirred rapidly at this temperature for one hour and allowed to cool under a nitrogen atmosphere.

To a five liter flask containing 3300 ml xylene is added 12 g of activated carbon (Darco G-60) and the mixture heated at reflux while collecting xylene/water in a separator/decanter. To this is added one half of the above xylene slurry of the intermediate compound of formula (I) obtained above. The mixture is brought to reflux and methanol/xylene distilled off at a rate of 25 ml per hour while adding fresh xylene to maintain a reaction volume of about 3500 ml. After four hours, one third of remaining slurry of the intermediate compound is added and methanol/xylene distillation resumed at the same rate. The remaining portions (one third or remainder) of intermediate are added at 8 hours and 12 hours, respectively, and the distillation continued at 25 ml/hour for a total of 16 hours. After 16 hours the distillation rate is decreased to 12.5 ml per hour for a total of 34 hours.

The reaction mixture is cooled to about 100° C., and filtered to remove carbon, washing the carbon cake with 100 ml warm xylene. The filtrate is purged with nitrogen, cooled to 25°–50° C. with rapid stirring. Stirring is continued for one hour to allow for complete crystallization. The crystals are collected by filtration, the mother liquor concentrated to about 1500 ml, cooled under nitrogen to 0°–5° C., filtered, the cake is washed with 100 ml cold xylene and the crystalline product dried under vacuum below 60° C. The yield of piroxicam is 121–132.8 g (82–90% of theory). Average throughput, 38.5 g/liter of solvent.

B. The above procedure is repeated but with the following modifications:

To 600 ml of mixed xylene, under a nitrogen atmosphere is added 160 g (0.594 mole) methyl 3,4-dihydro-2-methyl-4-oxo-2H-1,2-benzothiazine-3-carboxylate-1,1-dioxide and 60 g (0.637 mole) technical grade 2-aminopyridine. The mixture is heated at 85°–90° C. for two hours, cooled to 20°–25° C. and stirred at this temperature for 2 hours. The resulting crystalline intermediate is collected by filtration and washed with 100 ml cold xylene. A weighed sample of the solvent-wet crystals was dried in vacuo. Differential scanning calorimetry of the dry sample gave a single sharp peak at 132.9° C. From the weight of dried sample it is determined that the yield of intermediate of formula (I), R=R¹=CH₃,

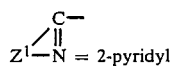

is 215.9 g (98%).

To 3300 ml of mixed xylenes is added 3 g of 2-aminopyridine, 8 g of activated carbon (Darco KBB), the mixture is heated to a gentle reflux while collecting xylene/water until system is devoid of moisture. Then 81 g (dry weight basis) (0.223 mole) of the above crystalline intermediate mixed with 50 ml xylene is added. The reaction mixture is heated at reflux while separating methanol/xylene at a rate of 25 ml/hour. Every two hours an additional 17 g intermediate is added until all of the 215.9 g obtained above is consumed. This requires about 16 hours. Refluxing at 25 ml/hour is continued until the 20 hour mark at which time the reflux rate is reduced to 12–13 ml/hour. The total reaction volume is maintained between 3.3 and 3.7 liters by addition of xylene as required. After a total reaction time of 34 hours, the mixture is cooled and the product isolated as in Part A, above to provide 165.3 g (84%) of piroxicam. Throughput, 50 g/liter of solvent.

EXAMPLE 8

Comparison of Standard and Improved Piroxicam Processes Employing Recycling of Mother Liquors The Standard Method (Example 6) and the Improved Method (Example 7) were each repeated four times with recycling of the mother liquor from the previous run in each of the 2nd, 3rd and 4th runs. Results are summarized below.

| Run No. | % Yield Standard Method with Recycle | % Yield Improved Method with Recycle |
| --- | --- | --- |
| 1 | 81 | 83 |
| 2 | 90 | 87 |
| 3 | 93 | 96 |
| 4 | None | 93 |
| Av. over 4 Runs | 66 | 90 |

At each stage of this recycle experiment the batches employing the Standard Method had higher color levels, which became progressively more marked. In the fourth run by the Standard Method only a syrup was obtained which could not be induced to crystallize. The Improved Method, by contrast, gave a 93% yield in the fourth run. The experiment was terminated at this point because the Standard Method afforded no product. After the fourth run by the Improved Method the mother liquor was still clear and, it is assumed, could be used in further runs to good advantage.

EXAMPLE 9

When the procedures of Examples 7 and 8 are repeated but employing the appropriate compound of formula (I), provided in Example 3, as intermediate, the following products of formula (IV) are also obtained in improved yield and throughput.

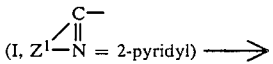

-continued

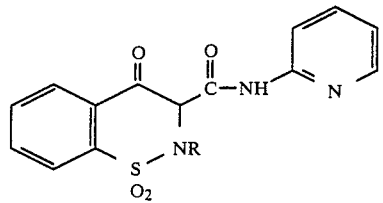

(IV, Z = 2-pyridyl)

where R and $R^1$ are as defined in Example 3.

EXAMPLE 10

Employing the compounds of formula (I) provided in Examples 4 and 5 as starting material in the procedure of Example 7 and in the recycling procedure of Example 8, the following products of formula (IV) are also obtained in improved yield and throughput.

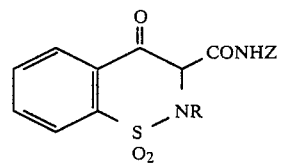

where R and Z are as defined in Examples 4 and 5.

EXAMPLE 11

Improved Sudoxicam Process Employing Intermediate (I, $R=R^1=CH_3$,

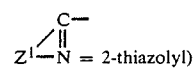

A flask containing 30 ml xylene and 0.5 g of the crystalline 2-thiazolyl intermediate of formula (I), obtained previously, is slowly distilled at the rate of 5 ml per 2.5 hours. Xylene (5 ml) and 0.25 g of intermediate are then added and the distillation repeated as above. It is then repeated one more time after which the mixture is subjected to total reflux for 7 hours. The mixture is then stirred at ambient temperature over the weekend (~60 hours) and filtered to remove the product Sudoxicam, the 2-thiazolyl analog of Piroxicam, in 65% yield (590 mg), m.p. 245°–247° C. (dec).

I claim:

1. A process for production of a 3,4-dihydro-2H-1,2-benzothiazine-3-carboxamide-1,1-dioxide of the formula

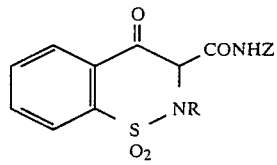

wherein R is hydrogen, benzyl or alkyl having from one to three carbon atoms; and Z is 2-pyridyl, alkyl substituted-2-pyridyl, 2-thiazolyl, 2-thiazolyl substituted by one or two alkyl groups, or 5-alkyl-3-isoxazolyl, each alkyl having from one to four carbon atoms; which comprises the steps of:

(a) contacting an ester of the formula

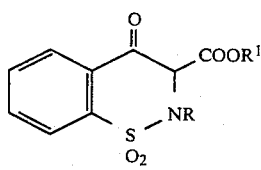

wherein $R^1$ is benzyl or alkyl having from one to four carbon atoms, with an amine of the formula $ZNH_2$ in the presence of reaction inert organic solvent at a temperature of from about 50°–110° C., to provide an intermediate compound of the formula

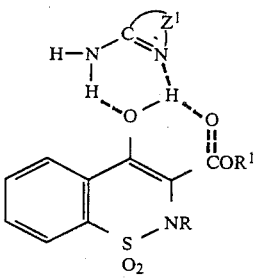

(b) isolating the intermediate compound and heating said intermediate in the presence of reaction inert organic solvent at a temperature of from about 120°–200° C.

2. A process according to claim 1 wherein R is methyl and $R^1$ is methyl or ethyl.

3. A process according to claim 2 wherein Z is 2-pyridyl, 2-thiazolyl, 5-methyl-3-isoxazolyl, 6-methyl-2-pyridyl or 4,5-dimethyl-2-thiazolyl.

4. A process according to claim 3 wherein Z is 2-pyridyl and $R^1$ is methyl.

5. A process according to claim 1 wherein in step (a) said reaction is carried out at 20°–90° C.

6. A process according to claim 1 wherein in step (b) said temperature is from about 135°–145° C.

7. A process according to claim 1 wherein the product of step (b) is isolated and the mother liquor is recycled.

8. A process according to claim 1 wherein said reaction inert organic solvent is xylene.

9. A process according to claim 1 wherein a technical grade of amine $ZNH_2$ is employed in step (a).

10. A process according to claim 9 wherein Z is 2-pyridyl.

11. A process according to claim 10 wherein a crystalline intermediate is isolated in step (b).

* * * * *

UNITED STATES PATENT AND TRADEMARK OFFICE
CERTIFICATE OF CORRECTION

PATENT NO. : 4,536,573
DATED : August 20, 1985
INVENTOR(S) : Joseph A. Kardys

It is certified that error appears in the above-identified patent and that said Letters Patent is hereby corrected as shown below:

In the Abstract, change formula (I) to read:

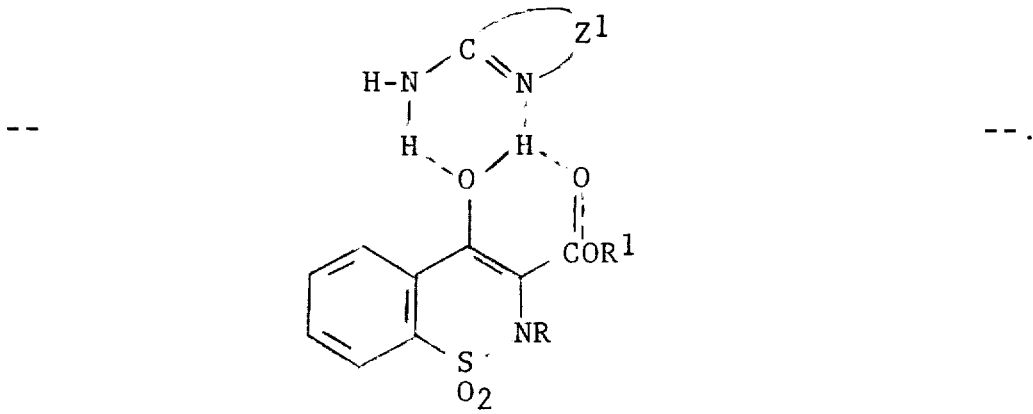

UNITED STATES PATENT AND TRADEMARK OFFICE
CERTIFICATE OF CORRECTION

PATENT NO. : 4,536,573
DATED : August 20, 1985
INVENTOR(S) : Joseph A. Kardys

It is certified that error appears in the above-identified patent and that said Letters Patent is hereby corrected as shown below:

Column 10, line 14, change the formula to read:

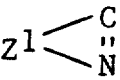

-- (I, R = R$^1$ = CH$_3$, Z$^1$⟨C‖N = 2-pyridyl) --.

Signed and Sealed this

Twenty-eighth Day of January 1986

[SEAL]

Attest:

DONALD J. QUIGG

Attesting Officer

Commissioner of Patents and Trademarks